United States Patent [19]

Wagner

[11] Patent Number: 5,671,633

[45] Date of Patent: Sep. 30, 1997

[54] PLATE ARRAY FOR MOISTURE SENSOR WITH REDUCED SENSITIVITY TO LOADING EFFECTS

[75] Inventor: Edward Duane Wagner, Rogue River, Oreg.

[73] Assignee: Wagner Electronic Products, Inc., Rogue River, Oreg.

[21] Appl. No.: 600,303

[22] Filed: Feb. 12, 1996

[51] Int. Cl.[6] .................................................. G01N 27/02
[52] U.S. Cl. ........................................... 73/73; 324/688
[58] Field of Search ................................ 324/664, 668, 324/688; 73/73

[56] References Cited

U.S. PATENT DOCUMENTS

| 3,515,987 | 6/1970 | Zurbrick et al. | 324/688 X |
| 3,959,723 | 5/1976 | Wagner | 324/688 X |
| 4,563,635 | 1/1986 | Wagner et al. | 324/688 |
| 4,845,421 | 7/1989 | Howarth et al. | 324/688 |

FOREIGN PATENT DOCUMENTS

| 440614 | 8/1974 | U.S.S.R. | 324/688 |

Primary Examiner—William A. Cuchlinski, Jr.
Assistant Examiner—Willie Morris Worth
Attorney, Agent, or Firm—Klarquist Sparkman Campbell Leigh Whinston LLP

[57] ABSTRACT

A plate array for moisture sensors has a transmitter electrode and a detector electrode interposed between portions of a phase electrode. The transmitter and phase electrodes are driven with alternating current signals having a one hundred and eighty degree phase difference so as to induce a signal at the detector electrode relating to a moisture content of a material in the electrical fields which has a reduced sensitivity to electrically loading the material, such as from contact with a hand or steel roller.

10 Claims, 4 Drawing Sheets

PLATE ARRAY FOR MOISTURE SENSOR WITH REDUCED SENSITIVITY TO LOADING EFFECTS

FIELD OF THE INVENTION

This invention relates to an array or configuration of electrodes in a moisture content sensor.

BACKGROUND AND SUMMARY OF THE INVENTION

In some prior moisture sensors, the moisture content of a material is sensed by passing the material through an electrical field generated by applying an alternating current signal to a transmitter electrode. When the material is passed through the field, the material becomes a conductor of the field. A detector electrode is positioned near the transmitter plate. The material conducts a portion of the electrical field proportional to the material's dielectric constant (which, in turn, relates to the material's moisture content) to the detector plate. This induces a signal at the detector electrode related to the moisture content of the material.

In certain of these prior moisture sensors, a phase electrode is interposed between the transmitter and detector electrodes and driven with a phase signal. The phase signal typically is an alternating current signal which is shifted one hundred and eighty degrees in phase and has a reduced magnitude in comparison to the transmitter signal. This has the effect of shaping the electrical field generated by the transmitter electrode to project farther out from the transmitter and detector electrodes and into the material under test. This also acts to reduce sensitivity to moisture at the surface of the material under test ("surface moisture").

For example, a typical transmitter-phase-detector plate configuration for end-to-end moisture sensors is formed by etching a copper-plated surface of a fiberglass circuit board to define three side-by-side bar shaped areas of the copper-plated surface that are the transmitter, phase and detector electrodes, respectively. The typical end-to-end moisture sensor has two such boards with this plate configuration mounted in parallel above and below a space through which material (such as wood) is fed end-to-end by hand, or on belts or rollers. The plate configurations on the boards project the electrical field into the space between them through which the material is fed to sense the material's moisture content.

A remaining problem with this prior plate configuration is its sensitivity to electrical loading effects. Often the ends of the material being fed through the end-to-end moisture sensor is coupled to ground, such as when an end of the material is grasped by hand or is fed through the moisture sensor by steel rollers. This, in effect, places a resistive load on the material which can increasingly conduct away a portion of the electrical field projected by the transmitter plates as the moisture content of the material increases, and consequently counteract the effect of the increase in moisture content on the signal at the detector electrodes. Thus, while the signal at the detector electrodes initially increases as the moisture content of the material increases up to a saturated moisture content (e.g., 40–50% moisture content), this loading effect can cause the detector electrodes' signal to begin decreasing for increases in the actual moisture content above the saturated level. As a result, the moisture sensor may incorrectly show that heavily saturated materials are dry.

The present invention is a plate or electrode array for moisture sensors with reduced sensitivity to these electrical loading effects. The plate array comprises a transmitter electrode and a detector electrode interposed between or inside a phase electrode or phase electrodes. The transmitter electrode is driven with an alternating current transmitter signal to produce an electrical field in which a material can be placed to induce a signal at the detector electrode which is related to the moisture content of the material. The phase electrodes are driven with a phase signal which is approximately one hundred and eighty degrees out of phase with the transmitter signal. Since the phase electrode or electrodes are positioned outside the transmitter and detector electrodes, this acts to block the electrical field generated by the transmitter electrode from being conducted outside a space generally bounded by the phase electrodes. Consequently, grounding or loading a portion of the material which is outside this space has a much reduced effect on the moisture content-related signal induced at the detector electrode.

In the illustrated embodiment of the invention, the electrodes are formed as four elongated, generally bar-shaped conductors supported on a planar surface of a substrate. The two inner conductors are the transmitter and the detector electrodes, while the two outer conductors are the phase electrodes. The width or area of the phase electrode which is adjacent the transmitter electrode is greater than that of the phase electrode which is adjacent to the detector electrode to more effectively block conduction of the electrical field on the transmitter electrode side of the plate array outside the space.

Additional features and advantages of the invention will be made apparent from the following detailed description of an illustrated embodiment which proceeds with reference to the accompanying drawings.

DETAILED DESCRIPTION OF THE ILLUSTRATED EMBODIMENTS

Figure 1:
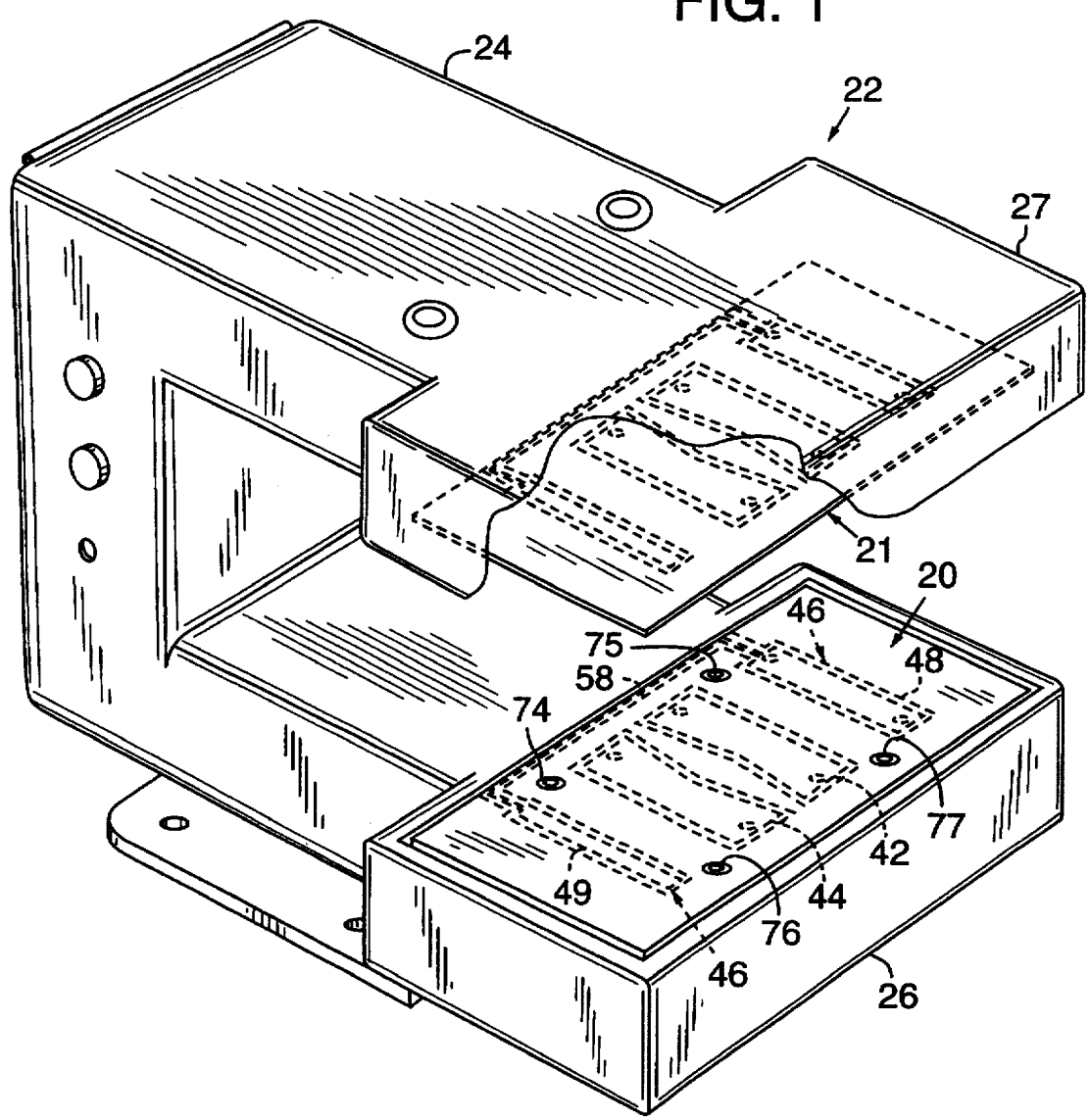
FIG. 1 is a perspective view, partially cut away, of a housing of an end-to-end moisture sensor employing a plate array shown in FIG. 2.

Referring to FIG. 1, an illustrated embodiment of the invention is a plate array 20 for use (along with another plate array 21 configured in a mirror image to plate array 20) in an in-line moisture content sensor 22. The in-line moisture content sensor 22 comprises a housing 24 with lower and upper extentions ("jaws") 26–27. The plate array 20 is mounted on a top side of the lower jaw 26. While the mirror image plate array 21 is mounted on a bottom side of the upper jaw 27, parallel to and directly opposite the plate array 20 on the lower jaw 26.

Figure 2:
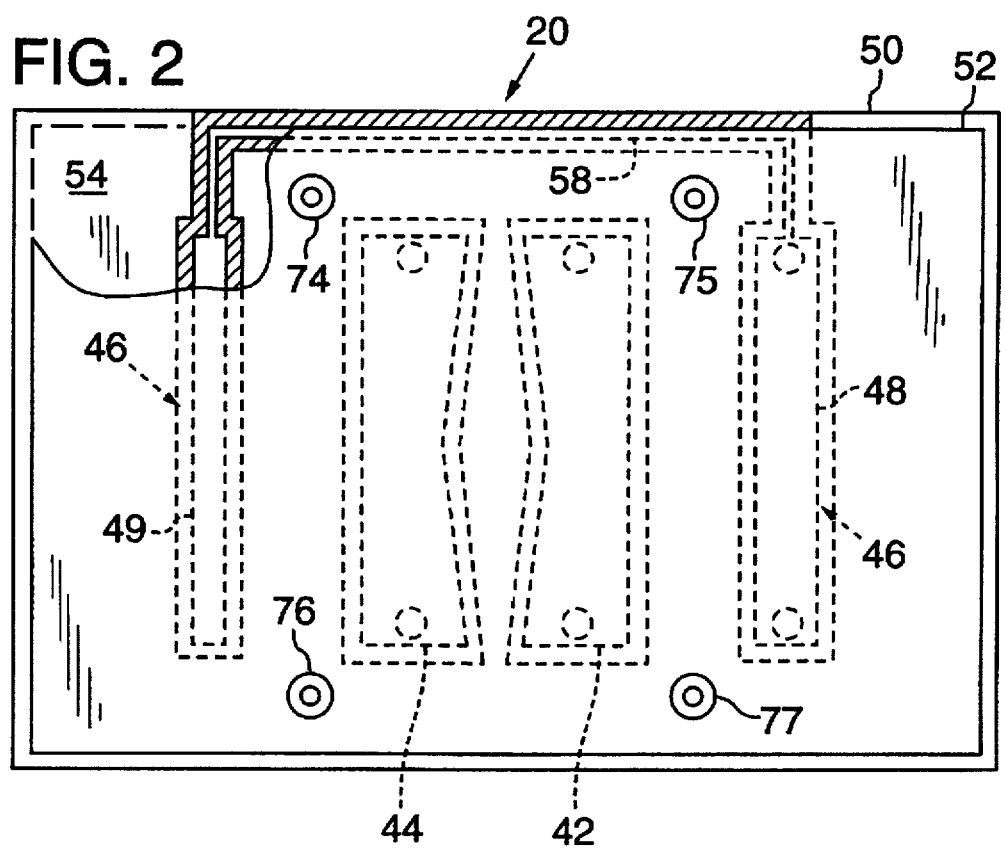
FIG. 2 is a cut-away top view of the plate array according to an illustrated embodiment of the invention.

With reference to FIG. 2, the illustrated plate array 20 (and likewise the mirror image plate array 21) is constructed as a multiple layer board having a transmitter electrode 42, a detector electrode 44, and a phase electrode 46 formed thereon. The transmitter electrode 42 and the detector electrode 44 are interposed between two portions 48–49 of the phase electrode to decrease the plate array's sensitivity to electrical loading effects as described more fully below.

The illustrated plate array 20 comprises a base layer or substrate 50 and a cover layer 52. The substrate 50 is a fiberglass circuit board with a copper-plated front and back surfaces 54–55 and dimensions of approximately 7.625 inches long, 5.25 inches wide, and 0.125 inches thick. The cover layer 52 also is a fiberglass circuit board, but is not plated and has smaller dimensions of approximately 7.375 inches long, 5 inches wide, and 0.125 inches thick.

The electrodes 42, 44, and 46 are formed by etching the copper plated front surface 54 of the substrate 50 to define separated areas or conductor plates on the surface 54. The width of the etched areas separating the electrodes is approximately 0.125 inch. The conductor plates that form the electrodes are parallel, elongated, and generally bar-shaped copper-plated areas of the surface 54 remaining after etching. The inner conductor plates form the transmitter electrode 42 and the detector electrode 44. The transmitter electrode 42 and the detector electrode 44 are each approximately 3.25 inches in length and 0.875 inches in width, but gradually decrease in width towards the center of their innermost side (forming a v-shaped notch in the innermost side).

The outer conductor plates form the two portions 48–49 of the phase electrode 46. The portion 48 next to the transmitter electrode 42 is approximately 3.25 inches long by 0.5 inches wide, and separated from the transmitter electrode by approximately one inch. The portion 49 next to the detector electrode 44 is approximately 3.25 inches long by 0.25 inches wide, and separated from the detector electrode by approximately 1.062 inches. The portions 48–49 of the phase electrode are connected by a copper strip or trace 58 running near an edge of the substrate 50.

Figure 3:
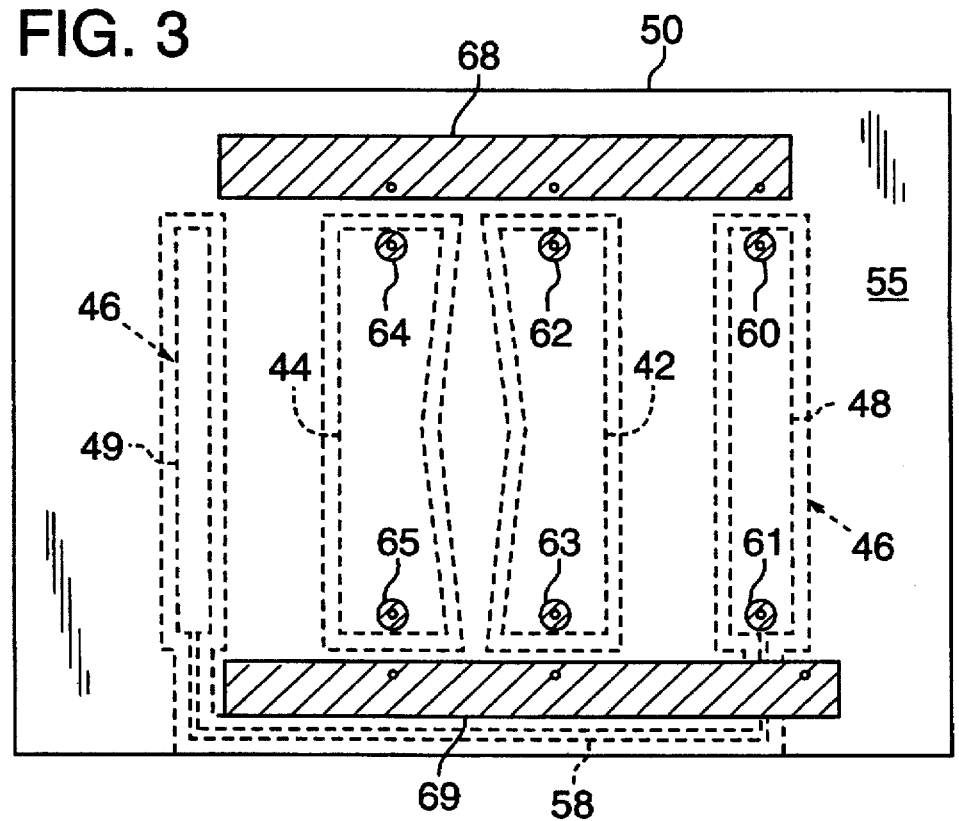
FIG. 3 is a back view of the plate array of FIG. 2.

Referring to FIG. 3, the copper-plated back surface 55 of the substrate 50 is etched to form connection pads 60 . 65 and ground pads 68–69. Two each of the connection pads 60 . 65 are connected respectively to the transmitter electrode 42, the detector electrode 44, and the portion 48 of the phase electrode 46 by metallized through holes. The connection pads 60 . 65 each are circular, and approximately 0.2 inches in diameter. Electrical connections are made to the connection pads to apply signals described below to the transmitter and phase electrodes 42, 46 and receive a moisture content related signal from the detector electrode 44.

The ground pads 68–69 have elongated bar shapes, and run near each longitudinal edge of the substrate 50. The ground pads are connected by metalized through holes to the remaining copper plating on the front surface 54 which separates and surrounds (except for the strip 58) the electrodes 42, 44, and 46. An electrical connection is made from the ground pads to ground.

Referring again to FIG. 2, the cover layer 52 is bonded over the front surface 54 of the substrate 50 with an adhesive or the like to form the multi-layered board construction of the plate array 20. With this arrangement, the electrodes 42, 44 and 46 are sandwiched between the substrate layer 50 and the cover layer 52. This protects the electrodes from being damaged in use. Because of the smaller dimensions of the cover layer 52, the multi-layered plate array 20 has a step of approximately 0.125 inches width along each edge. A set of four holes 74–77 for mounting screws are drilled through the plate array 20 for mounting the plate array to the housing 24 (FIG. 1).

Figure 4:
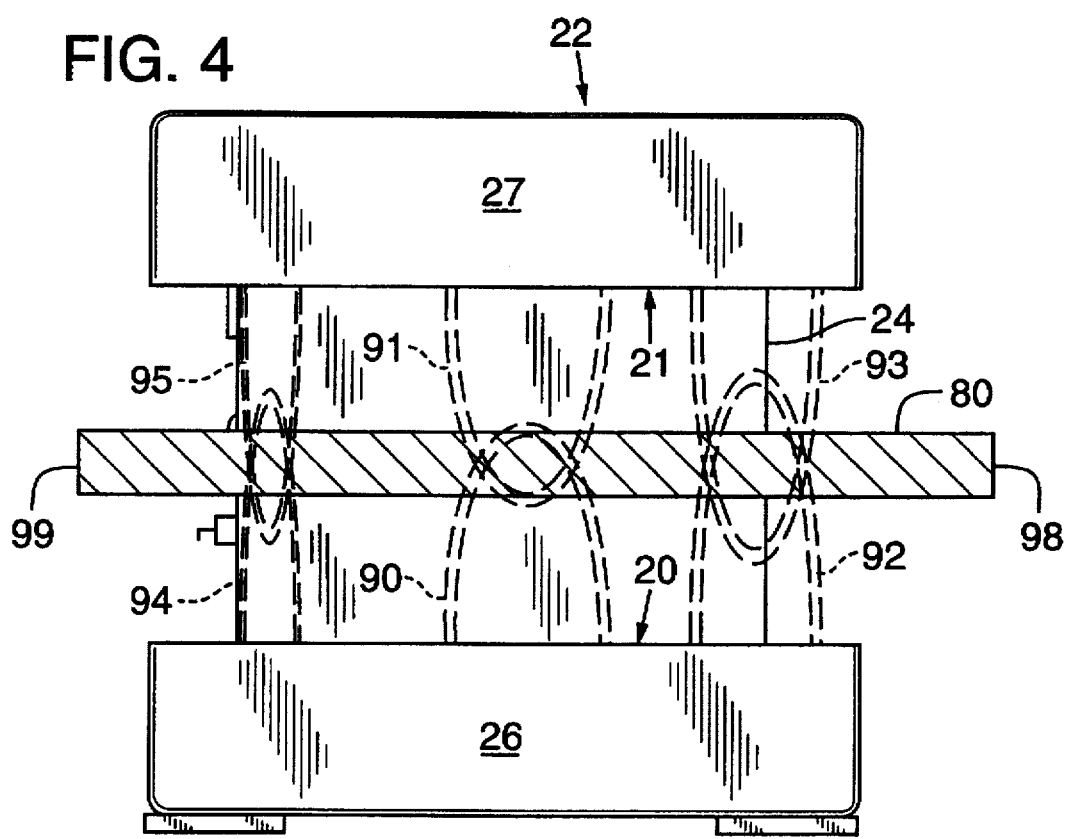
FIG. 4 is a front view of the end-to-end moisture sensor housing of FIG. 1 illustrating an electrical field and blocking electrical fields produced when transmitter and phase signals are applied to the plate array of FIG. 2.

Referring now to FIG. 4, in use, the in-line moisture content sensor 22 (FIG. 1) is placed in a production or manufacturing line of a material 80 or materials whose moisture content is to be monitored. Such moisture content monitoring is particularly important for materials for which variations in moisture content can result in degraded quality or manufacturing defects, such as wood products (e.g., lumber boards and sheets, furniture pieces, etc.). The materials are passed between the plate arrays 20–21 on the jaws 26–27 so as to sense their moisture content from end-to-end. Preferably, the materials are fed past the jaws 26–27 by automated equipment such as belts or rollers (not shown) to either side of the in-line moisture content sensor 22. For example, a piece of lumber 80 is shown being fed between the jaws 26–27 in FIG. 4. Although illustrated as a plate array for use in an in-line, end-to-end moisture sensor, it should be understood that plate arrays can be configured according to alternative embodiments of the invention for other types of moisture content sensing devices and applications, such as side-to-side in-line moisture sensors, hand-held moisture sensors, and probe type (i.e., for insertion in stacked materials) moisture sensors, among others.

Figure 5:
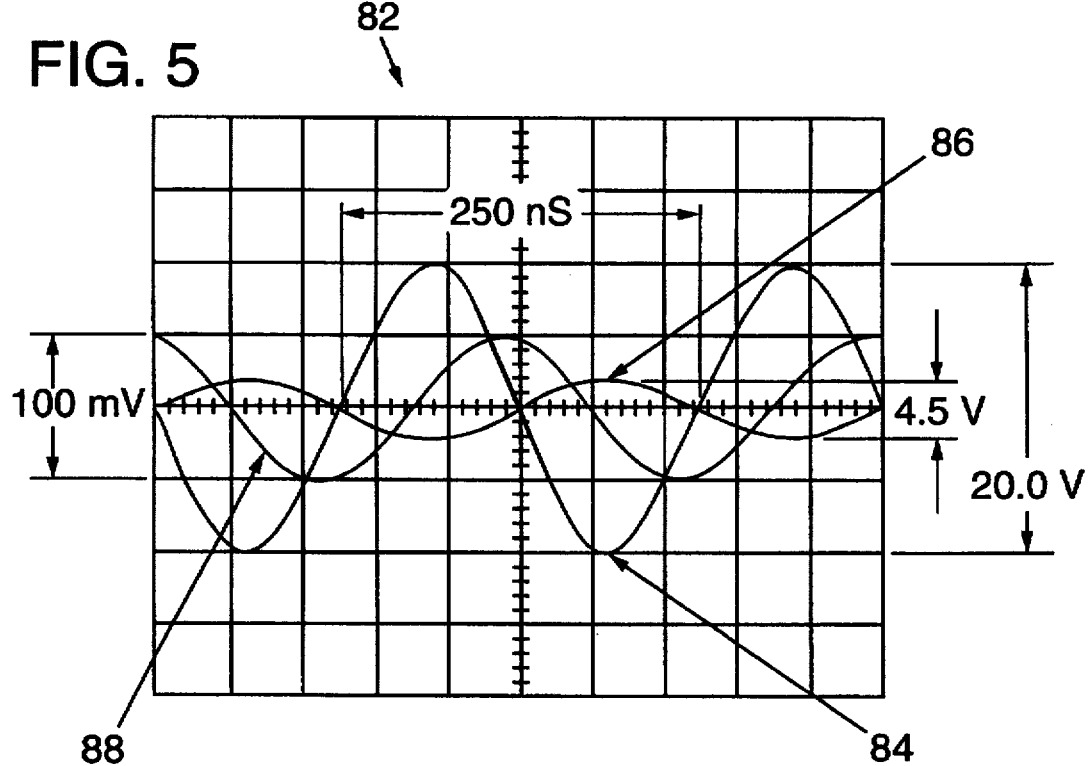
FIG. 5 is a wave form diagram of a transmitter signal and phase signals applied to the plate array of FIG. 2 and a resulting baseline detector signal produced by the plate array.
Figure 6:
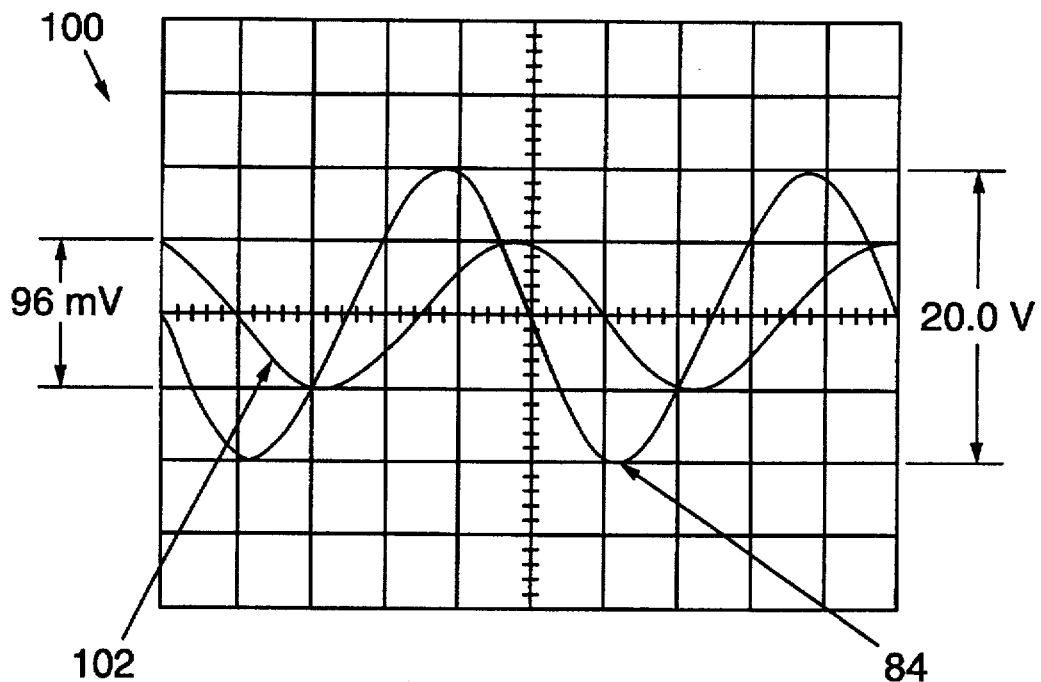
FIG. 6 is a wave form diagram of a transmitter signal and phase signals applied to the plate array of FIG. 2 and a resulting detector signal produced by the plate array for a 1 by 4 inch size piece of Douglas Fir lumber having an 11.5% moisture content.
Figure 7:
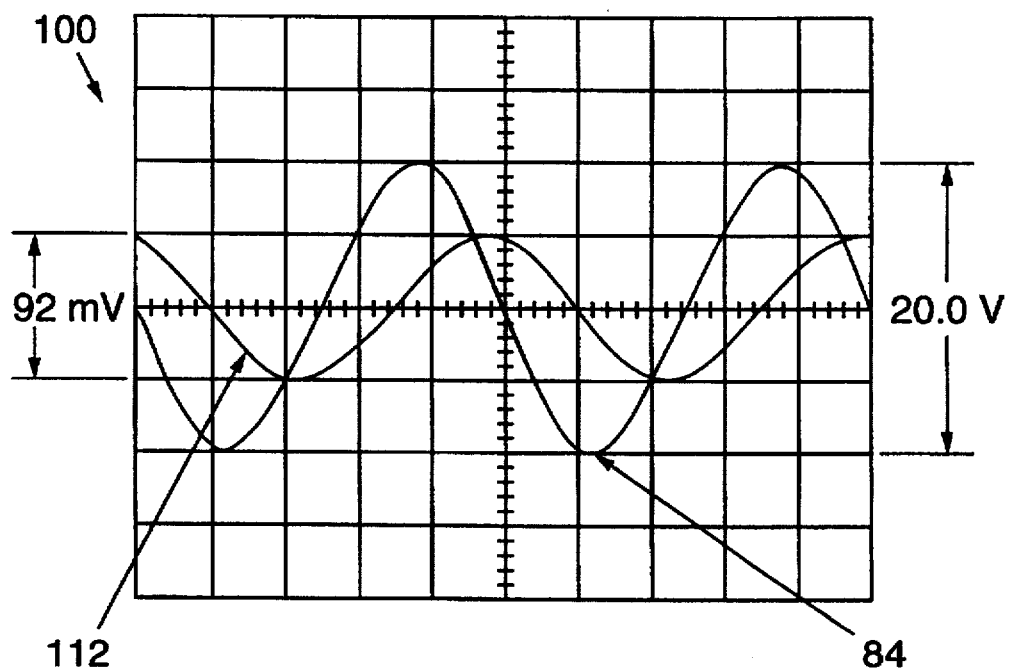
FIG. 7 is a wave form diagram of a transmitter signal and phase signals applied to the plate array of FIG. 2 and a resulting detector signal produced by the plate array for a 1 by 4 inch size piece of Douglas Fir lumber having an 24% moisture content.

With reference to FIGS. 4 and 5, the transmitter and phase electrodes 42, 44 are driven with a transmitter signal 84 and a phase signal 86, respectively. As depicted in a wave form diagram 82 of voltage versus time, the transmitter signal 84 in the illustrated embodiment is an alternating current signal with a sinusoidal wave form, a 4 MHz frequency, and a 20 volt peak-to-peak amplitude. The phase signal also is a alternating current signal with a sinusoidal wave form, and a 4 MHz frequency. The phase signal, however, has a reduced magnitude of 4.5 volts peak-to-peak and a phase difference of 180 degrees as compared to the transmitter signal.

Referring again to FIG. 4, when driven with the transmitter signal 84, the transmitter plates 42 on the plate arrays 20, 21 produce electrical fields 90–91 which overlap in the space between the plate arrays through which the lumber 80 passes. The phase plates 46 on the plate arrays 20–21 produce counteracting electrical fields 92–95 at the ends of the plate arrays which act to block or reduce the amount of the electrical fields 90–91 conducted for high moisture contents of the lumber 80 to an electrical load (e.g., a connection to ground, such as from contact with a worker's hand or steel roller) at either end 98–99 of the lumber 80. The electrical fields 92–95 thus effectively form a boundary to the electrical fields 90–91.

As discussed above with reference to FIG. 2, the portion 48 of the phase electrode 46 which is nearer to the transmitter electrode 42 is formed with a greater area or width than the portion 49 to the other side of the detector electrode 44. This compensates for the portion 48 being nearer the transmitter electrode 42 by projecting the transmitter-side counteracting electrical fields 92–93 to have a greater strength than the detector-side counteracting electrical fields 94–95. The greater strength of the electrical fields 90–91 near the transmitter electrode 42 would otherwise be more readily conducted to an electrical load placed at the transmitter side end 98 of the lumber 80.

The detector electrode 44 in the illustrated embodiment is electrically coupled to a tank circuit which comprises a 1 KΩ resistor, a 2.2 µH inductor, a 620 pF capacitor, and a 100 pF capacitor in a parallel connection between the detector electrode 44 and ground. With this connection, the electrical fields 90,91 induce a detector signal (e.g., signals 88, 102, 112) at the detector electrode 44 related to the dielectric constant of any material within the electrical fields 90, 91 between the transmitter electrode 42 and the detector electrode 44. Since the dielectric constant of materials generally vary with their moisture content, the signal induced at the detector electrode 44 varies in relation to the moisture content of the material. (In effect, the tank circuit operates to compensate for the capacitance between the transmitter electrode 42 and the detector electrode 44, forming essentially a resistive or voltage divider network comprising the moisture content-related resistivity between the electrodes. 42, 44 and the 1 KΩ resistor.) The wave form diagrams 88, 100, and 110, for example, show detector signals 98, 102 and 112 for baseline (i.e., no material between the plate arrays 20, 21), a 1×4 sized douglas fir lumber with an 11.5% moisture content, and a 1×4 sized douglas fir lumber with a 24% moisture content, respectively.

Having described and illustrated the principles of my invention with reference to an illustrated embodiment, it will be recognized that the illustrated embodiment can be modified in arrangement and detail without departing from such principles. It should be understood that the programs, processes, or methods described herein are not related or limited to any particular type of computer apparatus, unless indicated otherwise. Various types of general purpose or specialized computer apparatus may be used with or perform operations in accordance with the teachings described herein. Elements of the illustrated embodiment shown in software may be implemented in hardware and vice versa.

In view of the many possible embodiments to which the principles of my invention may be applied, it should be recognized that the detailed embodiments are illustrative only and should not be taken as limiting the scope of my invention. Rather, I claim as my invention all such embodiments as may come within the scope and spirit of the following claims and equivalents thereto.

I claim:

1. A plate array for a moisture content sensor, comprising:
   a substrate;
   a transmitter electrode supported on the substrate and producing an electrical field in a surrounding space when driven by an alternating current transmitter signal;
   a detector electrode supported on the substrate next to the transmitter electrode such that a signal related to a moisture content of a material placed in the electrical field is induced in the detector electrode;
   a phase electrode having a first portion and a second portion supported on the substrate and having the transmitter electrode and the detector electrode interposed between the portions of the phase electrode,
   whereby driving the phase electrode with a phase signal that is substantially one hundred and eighty degrees out of phase with the transmitter signal reduces the effects of electrically loading the material on the moisture-related signal.

2. The plate array of claim 1 wherein one of the portions of the phase electrode is positioned closer to the transmitter electrode, and has a greater area so as to compensate for the greater strength of the electrical field near the transmitter electrode.

3. The plate array of claim 1 wherein the transmitter electrode, the detector electrode, and the portions of the phase electrode comprise four elongated conductors which are each oriented laterally to a direction of travel of the material through the electrical field, the outer-most of the four conductors being the portions of the phase electrode, the first portion of the phase electrode being adjacent the transmitter electrode and having a greater width than the second portion to compensate for a greater strength of the electrical field near the transmitter electrode.

4. A plate array for a moisture content sensor, comprising:
   first and second opposed substrates having a space between for passing a material having a moisture content which is to be sensed;
   first and second detector electrodes formed one on each of the substrates;
   first and second transmitter electrodes formed one on each of the substrates;
   first and second phase electrodes formed one on each of the substrates and each having first and second portions to either side of the detector electrode and the transmitter electrode on the substrates;
   the transmitter electrodes on the substrates producing an electrical field in the space between the substrates when driven with an alternating current transmitter signal and causing a signal related to the moisture content of the material to be received at the detector electrodes; and
   the phase electrodes limiting the electrical field to the space bounded at one end by the first portions of the phase electrodes and at another end by the second portions of the phase electrodes when the phase electrodes are driven with an alternating current phase signal which is approximately one hundred and eighty degrees out of phase with the transmitter signal.

5. The plate array of claim 4 wherein each of the transmitter electrodes, the detector electrodes and the first and second portions of the phase electrodes each have an elongated shape and are oriented laterally to a direction of travel of the material through the space, the first portions of the phase electrodes being adjacent to the transmitter electrodes and having a greater width than the second portions of the phase electrodes.

6. The plate array of claim 4 wherein the substrates each have a planar surface on which the electrodes are supported, the planar surfaces of the substrates being parallel.

7. A method of configuring a plate array for a moisture sensor to have reduced sensitivity to electrical loading, comprising:
   positioning a transmitter electrode adjacent to a detector electrode such that a detector signal related to the moisture content of a material passed through an electrical field generated by applying an alternating current transmitter signal to the transmitter electrode is induced in the detector electrode;
   interposing the transmitter electrode and the detector electrode between two portions of a phase electrode such that driving the phase electrode with an alternating current phase signal which is substantially one hundred and eighty degrees out of phase with the transmitter signal reduces the effect on the detector signal of electrically loading the material outside a space bounded at two ends by the portions of the phase electrode.

8. The method of claim 7 further comprising:

positioning the transmitter electrode and the detector electrode between the first and second portions of the phase electrode with the transmitter electrode adjacent to the first portion of the phase electrode and the detector electrode adjacent to the second portion of the phase electrode; and forming the phase electrode with the first portion having a greater area than the second portion to counteract a greater strength of the electrical field near the transmitter electrode.

9. The method of claim 7 further comprising:

forming the transmitter electrode, the detector electrode and the portions of the phase electrode as elongated conductors supported on a planar substrate with the first portion adjacent to the transmitter electrode and the second portion adjacent to the detector electrode;

orienting the conductors lateral to a direction of travel of the material through the electrical field; and forming the first portion of the phase detector to have a greater width than the second portion so as to counteract a greater strength of the electrical field near the transmitter electrode.

10. The method of claim 7 further comprising:

supporting the transmitter electrode, the detector electrode and the phase electrode on a planar surface of a first substrate;

interposing a second transmitter electrode and a second detector electrode between first and second portions of a second phase electrode; and supporting the second transmitter electrode, the second detector electrode and the second phase electrode on a planar surface of a second substrate; and positioning the substrates with the planar surfaces in parallel and the electrodes on the substrates in mirror image such that the detector signal related to the moisture content of the material is induced in the detector electrodes on the substrates when the material is passed through an electrical field generated between the substrates by applying the transmitter signal to the transmitter electrodes on the substrates, and such that driving the phase electrodes on the substrates with the phase signal reduces the effect on the detector signal of electrically loading the material outside a space bounded at two ends by the portions of the phase electrodes.

* * * * *